(12) United States Patent
Hill (10) Patent No.: US 7,447,536 B2
(45) Date of Patent: Nov. 4, 2008

(54) SYSTEM AND METHOD FOR MEASUREMENT OF LOCAL LUNG FUNCTION USING ELECTRON BEAM CT

(75) Inventor: David Guy Hill, Danville, CA (US)

(73) Assignee: G.E. Medical Systems Global Technology Company, LLC, Waukesha, WI (US)

( * ) Notice: Subject to any disclaimer, the term of this patent is extended or adjusted under 35 U.S.C. 154(b) by 724 days.

(21) Appl. No.: 10/682,654

(22) Filed: Oct. 9, 2003

(65) Prior Publication Data
US 2004/0092811 A1 May 13, 2004

Related U.S. Application Data

(60) Provisional application No. 60/425,858, filed on Nov. 12, 2002.

(51) Int. Cl.
*A61B 5/05* (2006.01)
(52) U.S. Cl. .................. 600/413; 600/407; 600/428; 378/138; 378/4
(58) Field of Classification Search ......... 600/407–423, 600/429
See application file for complete search history.

(56) References Cited

U.S. PATENT DOCUMENTS

| | | | | |
|---|---|---|---|---|
| 4,352,021 A | * | 9/1982 | Boyd et al. ........... 378/12 |
| 4,521,900 A | | 6/1985 | Rand | |
| 4,521,901 A | | 6/1985 | Rand | |
| 4,625,150 A | | 11/1986 | Rand | |
| 4,644,168 A | | 2/1987 | Rand | |
| 4,773,087 A | * | 9/1988 | Plewes ............... 378/146 |
| 5,067,494 A | * | 11/1991 | Rienmueller et al. ... 600/428 |

(Continued)

FOREIGN PATENT DOCUMENTS

WO   WO 03/022134 A   3/2003

(Continued)

OTHER PUBLICATIONS

"Standardization of Spirometry, 1994 Update," American Thoracic Society, published in Am J. Respir. Crit. Care Med., vol. 152, pp. 1107-1136 (1995).

(Continued)

*Primary Examiner*—Brian L. Casler
*Assistant Examiner*—John F Ramirez
(74) *Attorney, Agent, or Firm*—McAndrews, Held & Malloy, Ltd.; Peter J. Vogel; Michael A. Dellapenna (57) ABSTRACT

Certain embodiments include a method and system for measuring and imaging local lung function. The method includes triggering an image scan of at least a lung cross-section of a patient, scanning the lung cross-section during at least one of an inspiration and an expiration of air by the patient to obtain lung image data and measuring a lung function during at least one of an inspiration and an expiration of air by the patient to obtain lung function data. The method may also include performing a preview scan of the patient to identify the lung cross-section for imaging. Additionally, the lung image data and lung function data may be combined for use in diagnosis of the patient. The lung image data and lung function data may also be output. The method may further include processing the lung function data to generate a plot of lung attenuation versus time.

20 Claims, 4 Drawing Sheets

U.S. PATENT DOCUMENTS

| | | | |
|---|---|---|---|
| 5,193,105 A | 3/1993 | Rand | |
| 5,289,519 A | 2/1994 | Rand | |
| 5,406,479 A | 4/1995 | Harman | |
| 5,719,914 A | 2/1998 | Rand | |
| 6,076,005 A | 6/2000 | Sontag et al. | |
| 6,208,711 B1 | 3/2001 | Rand | |
| 6,298,260 B1 * | 10/2001 | Sontag et al. | 600/413 |
| 2003/0051733 A1 * | 3/2003 | Kotmel et al. | 128/207.14 |
| 2003/0055331 A1 * | 3/2003 | Kotmel et al. | 600/410 |

OTHER PUBLICATIONS

"Lung Function Testing: Selection of Reference Values and Interpretative Strategies," American Thoracic Society, published in Am. Rev. Respir. Dis., vol. 144, pp. 1202-1218 (1991).

* cited by examiner

SYSTEM AND METHOD FOR MEASUREMENT OF LOCAL LUNG FUNCTION USING ELECTRON BEAM CT

CROSS REFERENCE TO RELATED APPLICATIONS

This is a non-provisional utility patent application claiming priority to provisional application No. 60/425,858 filed on Nov. 12, 2002.

BACKGROUND OF THE INVENTION

The present invention generally relates to imaging with an Electron Beam Tomography (EBT) scanner. In particular, the present invention relates to measuring local lung function using an EBT scanner.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of a subject, such as a patient, for example, through exposure to an energy source, such as x-rays passing through a patient. The generated images may be used for many purposes. For instance, internal defects in a subject may be detected. Additionally, changes in internal structure or alignment may be determined. Fluid flow within a subject may also be represented. Furthermore, the image may show the presence or absence of components in a subject. The information gained from medical diagnostic imaging has applications in many fields, including medicine and manufacturing.

EBT scanners are generally described in U.S. Pat. No. 4,352,021 to Boyd, et al. (Sep. 28, 1982), and U.S. Pat. No. 4,521,900 (Jun. 4, 1985), U.S. Pat. No. 4,521,901 (Jun. 4, 1985), U.S. Pat. No. 4,625,150 (Nov. 25, 1986), U.S. Pat. No. 4,644,168 (Feb. 17, 1987), U.S. Pat. No. 5,193,105 (Mar. 9, 1993), U.S. Pat. No. 5,289,519 (Feb. 22, 1994), U.S. Pat. No. 5,719,914 (Feb. 17, 1998) and U.S. Pat. No. 6,208,711 all to Rand, et al., and U.S. Pat. No. 5,406,479 to Harman (Apr. 11, 1995). The above listed patents are referred to and incorporated herein by reference in their entireties.

As described in the above-referenced patents, an electron beam is produced by an electron source at the upstream end of an evacuated, generally conical shaped housing chamber. A large negative potential (e.g. −130 kV or −140 kV) on a cathode of the electron source accelerates the electron beam downstream along an axis of the housing chamber. Further downstream, a beam optical system that includes solenoid, quadrupole, and deflection coils focus and deflect the beam to scan along an x-ray producing target. EBT systems utilize a high-energy beam of electrons to strike the target and produce x-rays for irradiating an object to be imaged. The point where the electrons strike the target is called the "beam spot". The final beam spot at the target is shaped as an ellipse and must be suitably sharp and free of aberrations so as not to degrade definition in the image rendered by the scanner.

The x-rays produced by the target penetrate a patient or other object and are detected by an array of detectors. The detector array, like the target, is coaxial with and defines a plane orthogonal to the scanner axis of symmetry. The output from the detector array is digitized, stored, and computer processed to produce a reconstructed x-ray image of a slice of the object, typically an image of a patient's anatomy such as the heart or lungs.

An EBT scanner allows for the collection of many angles of view and scanning of a number of slices in a short time. There is no mechanically moving gantry. Both high resolution and dynamic scanning modes may be provided while eliminating the need for any target or detector motion by replacing conventional x-ray tubes with electron beam technology.

Multiple views may be generated by magnetically steering a focused electron beam along a 210-degree target ring positioned beneath a subject. Opposite the target ring is a stationary detector ring of cadmium tungstate crystals encompassing a 216-degree arc above the subject. Photodiodes in the detector ring are used for recording transmitted x-ray intensity. X-ray intensity data may be processed to produce an image.

One important function of medical diagnostic imaging is measurement of lung function and lung capacity. Lung measurements may be used to diagnose diseases and other problems associated with a patient's lungs or lung function. Lung information may be used to diagnose and treat such conditions as emphysema.

Typically, a spirometer or other device that measures air flow rate is used to obtain lung function measurements. A patient takes a deep breath in and rapidly expels the air or exhales. The spirometer measures a change in air volume in the lung over time. Unfortunately, using a spirometer in this manner measures function only for the entire lung. Additionally, measurement using a spirometer is a coarse measurement and does not allow detection of fine changes in lung function, such as early onset of disease. Thus, a system allowing early detection of disease in the lung would be highly desirable. Furthermore, a system that allows measurement of a portion of a lung, rather than the entire lung, would also be highly desirable.

A spirometer measures lung function while a patient inhales and then exhales rapidly, typically over a period of 1-2 seconds. That is, a spirometer measures a volume of air that a patient inhales or exhales as a function of time. A spirometer may also measure a flow or rate at which the volume is changing as a function of time. Measurements are currently obtained for an entire lung. However, no good imaging method currently exists to scan this rapid change in lung volume along with the spirometer. Conventional CT imaging systems are not fast enough to take images of local lung function. Prior art systems attempted to obtain EBT images every 500 ms with a 100 ms scan time. Since the length of a lung inhalation-exhalation maneuver is only approximately two seconds, use of 500 ms results in sampling of a patient's lungs that is too coarse (low level of detail) to diagnose developing disease or other condition in the lung. Alternatively, the prior art employs a scan every 116 ms, which results in excessive radiation exposure dosage, particularly for children, teenagers, and young adults. Thus, a system that may scan quickly enough to obtain images of local lung function would be highly desirable.

BRIEF SUMMARY OF THE INVENTION

Certain embodiments include a method and system for measuring and imaging local lung function. The method includes triggering an image scan of at least a lung cross-section of a patient, scanning the lung cross-section during at least one of an inspiration and an expiration of air by the patient to obtain lung image data and extracting from such images a lung function during at least one of an inspiration and an expiration of air by the patient to obtain lung function data. The method may also include performing a preview scan of the patient to identify the lung cross-section for imaging. Additionally, the lung image data and lung function data may be combined for use in diagnosis of the patient. The lung image data and lung function data may also be output. The method may further include processing the lung function data to generate a plot of lung attenuation versus time. The method may use the entire lung cross section and/or local lung regions (e.g., various lobes of the lung).

In a certain embodiment, the triggering step includes triggering the image scan based on air flow in the patient's lung. The scanning step may dynamically obtain the lung image data as at least one of air flow and air capacity in the lung are changing. Alternatively, the scanning step may obtain the lung image data with at least one of air flow and air capacity in the lung held constant. In a certain embodiment, the scanning step obtains lung image data during a sweep of at least 33 ms. In an alternative embodiment, the scanning step obtains lung image data during a sweep of at most 50 ms.

The system includes a trigger for triggering an imaging scan of the patient, an energy source for generating an electron beam to strike a target, and a target for producing radiation in response to the electron beam. The radiation irradiates at least a portion of the lung of the patient. The system also includes a detector for receiving the radiation after the radiation irradiates the lung of the patient during the imaging scan, a data acquisition system for obtaining lung image data from the detector based on the radiation, a reconstruction system for calculating cross sectional images from the image data, and an image manipulation system for combining the lung function data and the lung image data for use in diagnosis of the patient. Additionally, the system may include a spirometer for measuring function of a lung of a patient. The spirometer generates lung function data based on at least one of air flow and volume in said lung. The system may also include an output for at least one of displaying, printing, and storing the lung function data and the lung image data. The system may also transfer the lung function data and the lung image data to a workstation for further processing.

In a certain embodiment, the imaging scan is performed in an imaging sweep of at least 33 ms. In another embodiment, the imaging scan is performed in an imaging sweep of at most 50 ms. The reconstruction system may process the lung function data to generate a plot of lung attenuation versus time. The trigger may trigger the imaging scan based on the lung function data from the spirometer. The trigger may also trigger a preview scan of the patient to identify the portion of the lung for imaging scan. In a certain embodiment, the data acquisition system dynamically obtains the lung image data as at least one of air flow and air capacity in the lung are changing. Alternatively, the data acquisition system may obtain the lung image data with at least one of air flow and air capacity in the lung held constant.

Certain embodiments include a method for detecting lung abnormalities in a patient. The method includes obtaining lung function data based on at least one of air flow and air volume in a lung, triggering a scan of the lung based on the lung function data, scanning a cross-section of the lung to obtain a lung image in a single sweep, and examining the lung function data in conjunction with the lung cross-section image to detect abnormalities in the lung.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

For the purpose of illustration only, the following detailed description references certain embodiments of an Electron Beam Tomography (EBT) imaging system. It is understood that the present invention may be used with imaging systems other than EBT imaging systems.

Figure 1:
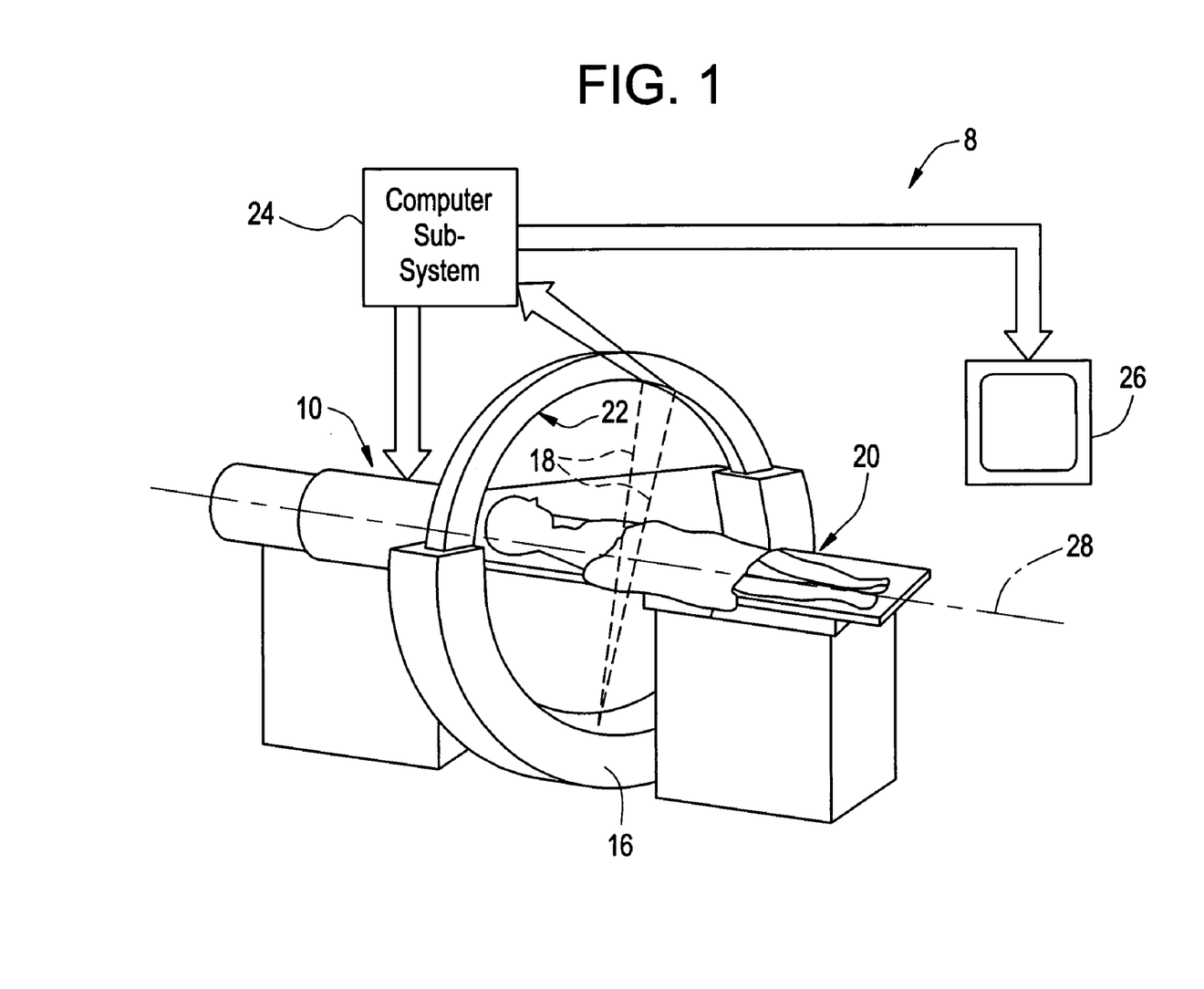
FIG. 1 illustrates an EBT imaging system that is used in accordance with an embodiment of the present invention.
Figure 2:
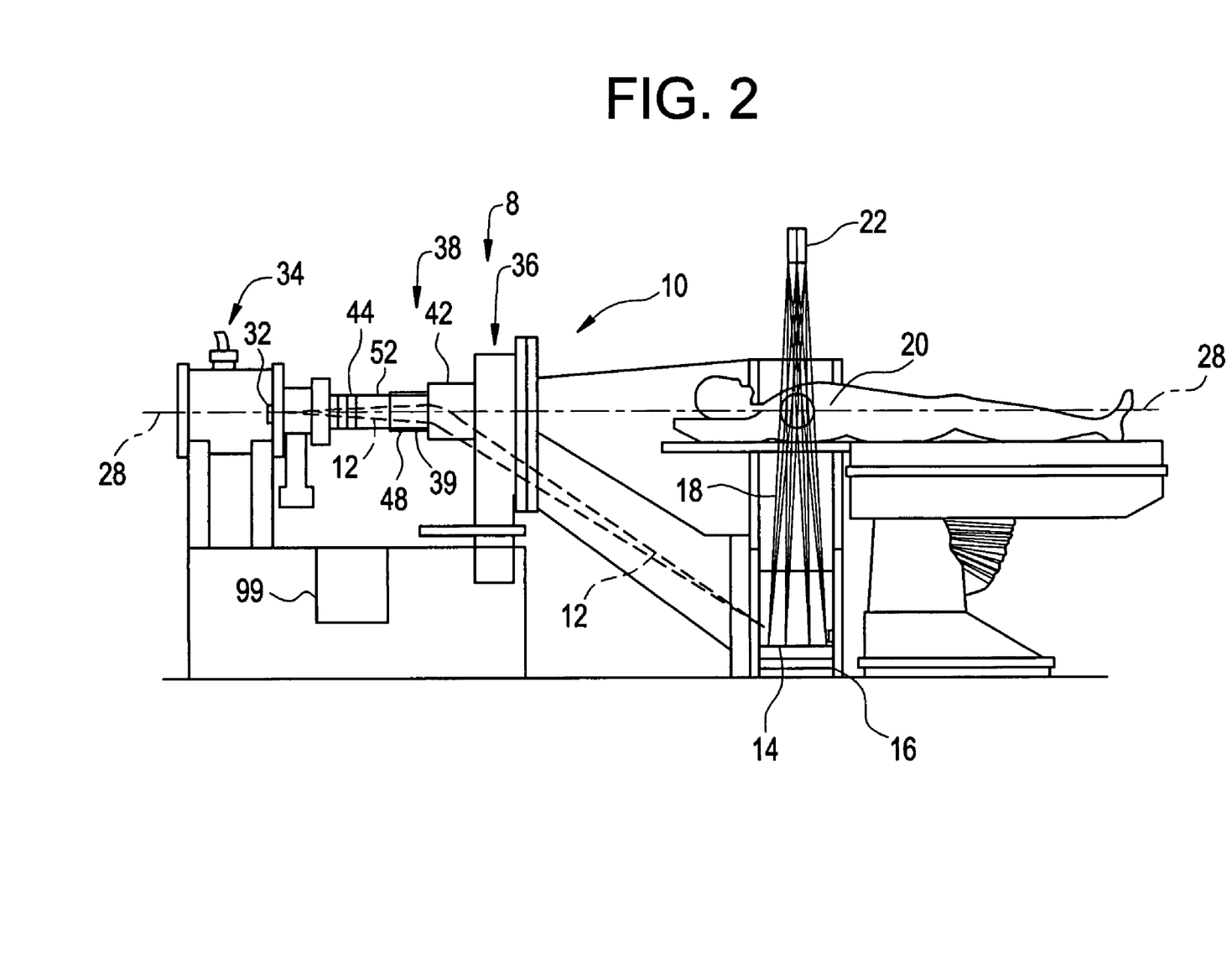
FIG. 2 illustrates a side view of an EBT imaging system, including an electron beam and x-ray emission path in accordance with an embodiment of the present invention.

Before describing certain embodiments of the present invention, it is helpful to understand the operation of an EBT imaging system. FIG. 1 and FIG. 2 illustrate an imaging system 8 formed according to an embodiment of the present invention. As shown in FIG. 2, system 8 includes a vacuum chamber housing 10 in which an electron beam 12 is generated at a cathode of an electron source 32 located in an upstream region 34, in response to a voltage, such as −140 kV. The electron beam 12 is then controlled by an optical system 38, including a magnetic lens 39 and a deflection coil 42, to scan at least one semi-circular target 14 located within a front lower portion 16 of the chamber housing 10.

When scanned by the focused electron beam 12, the target 14 emits a moving fanlike beam of x-rays 18. X-rays 18 then pass through a region of a subject 20 (a patient or other object, for example) and register upon a detector array 22 located diametrically opposite the target 14. Detector data is output to a processor or computer subsystem 24 that processes and records the data, producing an image of a slice of the subject on a video monitor 26. The computer subsystem 24 also controls the system 8 and electron beam production therein.

The beam optical system 38 is mounted within the chamber housing 10 and includes the magnetic lens 39, deflecting coils and quadrupole coils (collectively coils 42), and an electrode assembly 44. The lens 39 and coils 42 contribute a focusing effect to help shape a final beam spot into an elliptical shape as the electron beam scans one of the targets 14.

The electrode assembly 44 is mounted within the chamber housing 10 between the electron source 32 and the beam optical assembly 38 such that the electron beam 12 passes axially through the assembly 44 along the z-axis 28. The z-axis 28 is coaxial with the electron beam 12 upstream from the beam optics assembly 38 within the chamber housing 10. The z-axis 28 also may represent the longitudinal axis of the chamber housing 10 and the axis of symmetry for the electrode assembly 44 and the beam optics assembly 38 in accordance with an embodiment of the present invention. In another embodiment, the axis of the beam optics assembly 38 is angled with respect to the longitudinal axis of the chamber. The z-axis 28 is also typically the scanning axis through the subject 20 being scanned. However, in an embodiment, a surface on which the subject 20 is positioned may be tilted and slewed, making the z-axis 28 and the axis of the subject 20 not coincident.

To scan the subject 20, an x-ray fan beam 18 is rotated in the x-y plane through various positions or fan view angles. The center of the fan beam 18 is rotated through 210 degrees and is detected by an arc of detector elements, such as cadmium-tungstate crystal detector elements or other detector material, in the detector array 22. In an embodiment, each detector ring in the detector array 22 may include 1728 cadmium-tungstate crystal detector elements, for example. In an embodiment, the detector array 22 may include multiple coaxial rings with a varying number of detector elements and detector material. The fan beam 18 passes through the subject 20 within a reconstruction circle and impinges upon the detector array 22. Data samples obtained by a detector element in the detector array 22 over a single scan of the subject 20 constitute a detector fan. By way of example, the detector fan may include 864 data points or samples for a 50 ms scan. Each sample represents an x-ray path from the target 14 to a detector element that is attenuated by the subject 20. All data samples (all x-ray paths) collected over a scan from all detector elements (all detector fans) constitute a fan view sinogram.

Figure 3:
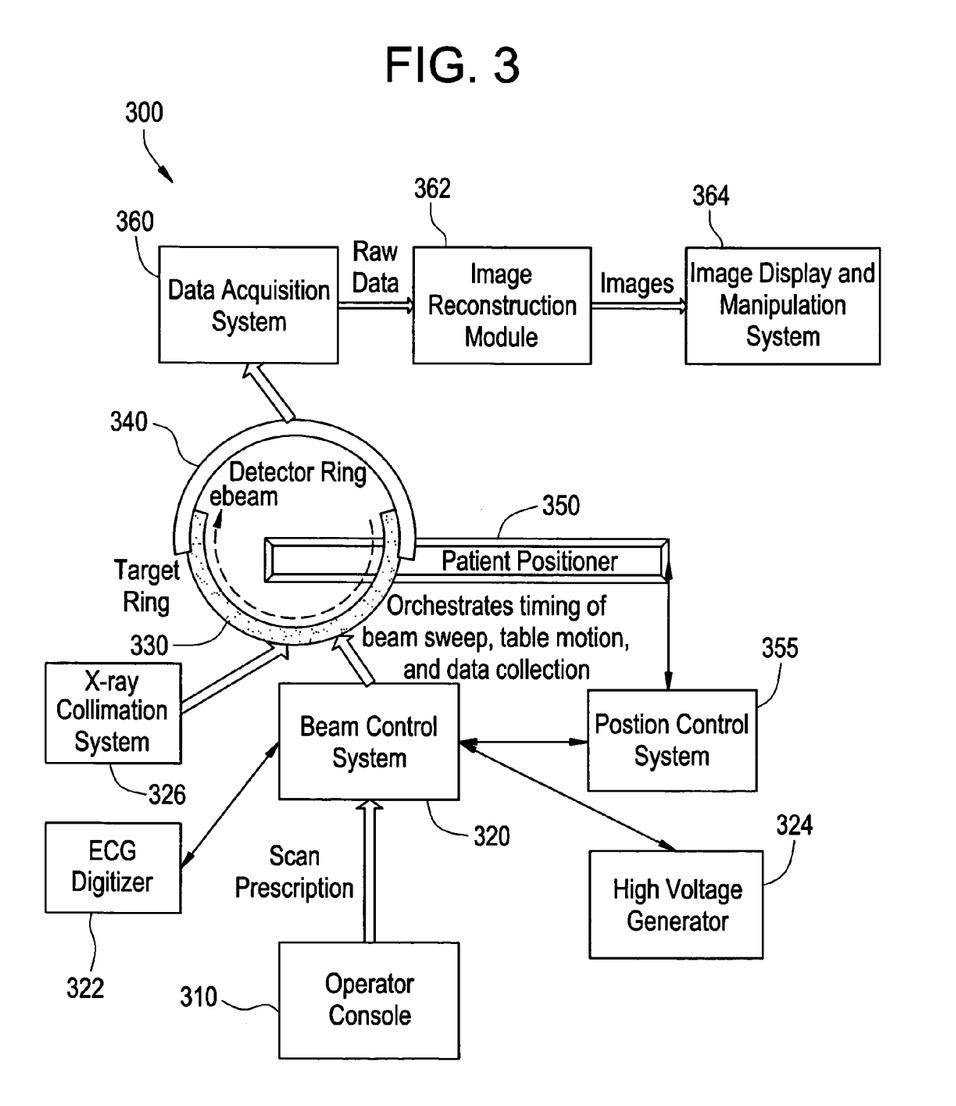
FIG. 3 illustrates a logical block diagram of an EBT imaging system in accordance with an embodiment of the present invention.

FIG. 3 illustrates a logical block diagram of an EBT imaging system 300 in accordance with an embodiment of the present invention. The system 300 includes an operator console 310, a beam control system 320, an ECG digitizer 322, a high voltage generator 324, an x-ray collimation system 326, a target ring 330, a detector ring 340, a patient positioner 350, a positioner control system 355, a data acquisition system (DAS) 360, an image reconstruction module 362, an image display and manipulation system 364, and a spirometer 370 (not pictured). The system 300 may also include an external workstation (not pictured) for manipulation and processing of image data. The workstation may derive functional curves from the image data.

The operator console 310, ECG digitizer 322, high voltage generator 324, and positioner control system 355 communicate with the beam control system 320 to generate and control an electron beam. The beam control system 320 communicates with the positioner control system 355 to control the patient positioner 350. The beam control system 320 causes the electron beam to sweep over the target ring 330. A sweep may be a single traversal of the target ring 330. The detector ring 340 receives radiation, such as x-ray radiation, for example, from the target ring 330. The DAS 360 receives data from the detector ring 340. The DAS 360 transmits data to the image reconstruction module 362. The image reconstruction module 362 transmits images to the image display and manipulation system 364. The components of the system 300 may be separate units, may be integrated in various forms, and may be implemented in hardware and/or in software.

The operator console 310 selects a mode of operation for the system 300. The operator console 310 may also input parameters or configuration information, for example, for the system 300. The operator console 310 may set parameters such as triggering, scan type, electron beam sweep speed, and patient positioner 350 position (for example, horizontal, vertical, tilt, and/or slew). An operator may input information into the system 300 using the operator console 310. Alternatively, a program or other automatic procedure may be used to initiate operations at the operator console 310. The operator console 310 may also control operations and characteristics of the system 300 during a procedure.

Based on operator input, the operator console 310 transmits operating information such as scanning mode, scanning configuration information, and system parameters, to the beam control system 320. In an embodiment, the ECG digitizer 322 transmits electrocardiogram trigger signals to the beam control system 320 to assist in timing of electron beam sweep and patient positioner 350 motion. An electrocardiogram (ECG) is a tracing of variations in electrical potential of a heart caused by excitation of heart muscle. An ECG includes waves of deflection resulting from atrial and ventricular activity changing with charge and voltage over time. A P-wave is deflection due to excitation of atria. A QRS complex includes Q-, R-, and S-waves of deflection due to excitation and depolarization of ventricles. An R-wave is an initial upward deflection of the QRS complex. A T-wave is deflection due to repolarization of the ventricles. The ECG digitizer 322 transmits ECG triggers based on one or more types of waves (such as the R-wave) to the beam control system 320 to assist in controlling the electron beam and imaging sweeps.

The system 300 may be configured to begin and end an imaging sweep based on the ECG triggers. The trigger points from the ECG data may be preprogrammed in the beam control system 320 and/or set by the operator console 310. Additionally, a scan may be manually triggered by the operator console 310 (by a push of a button, for example).

Data from the spirometer 370 or other measuring device may trigger a scan. The spirometer 370 is used to measure flow rates of a medium such as air. The spirometer 370 includes electronics to measure flow. The flow data may be converted (by software, for example) into a trigger that starts a scan. That is, a trigger may be created from a threshold set on air flow or air volume, for example. An external processor or a processor internal to the system 300 may process information from the spirometer 370 to produce a trigger.

Alternatively, any system or method detecting movement or change in a patient's chest may be used to trigger a scan. For example, light reflected from a mirror on the chest, a measure of impedance change in the chest, and/or a pneumatic belt around the chest may serve as a trigger. A user command may also trigger a scanning sequence concurrently with instructions to the patient to begin a breathing maneuver.

A typical lung examination involves a forced expiratory maneuver (rapidly exhaling air in the lungs) by the patient. The patient takes a deep breath, and the spirometer 370 measures the flow. When the patient rapidly releases his or her breath, the change in flow measured by the spirometer 370 starts the scan. The spirometer 370 trigger may be used in parallel with an ECG trigger or other trigger, such as a button trigger on the operator console 310. Scanning begins a few milliseconds, for example, after a trigger and samples regularly thereafter. For example, a scan may be a 50 ms scan occurring every 100 ms during a first second, every 200 ms during a second second, and once every 500 ms for seconds 3-6. If a shape of an overall volume-time curve demonstrates a slower rise, then the sampling ever 100 ms may be set to continue longer, for example.

For example, a pressure-sensitive switch may be connected between the spirometer 370 and the EBT beam control system 320 and/or the operator console 310. Expiration of air by the patient produces a pressure change that triggers both EBT 300 scanning and spirometer 370 measurement of a lung or lung segment. The lung image and lung function data may then be combined by the image reconstruction module 362 and/or the image display and manipulation system 364.

By way of example only, high temporal resolution 50 ms or 30 ms sweeps may be used to obtain a finer level of detail regarding lung material and lung function. Thus, onset of diseases such as emphysema may be detected earlier without significant increase in radiation exposure to the patient.

Higher temporal resolution also reduces motion artifacts appearing in the image. Certain embodiments provide arbitrary timing between sweeps to optimize sampling frequency between radiation dosage considerations and characterization of lung function and lung composition measurements.

The high voltage generator 324 may be used by the beam control system 320 to produce an electron beam. The high voltage generator 324 may be a Universal Voltronics or Spellman power supply with a power-on time of 80 or 130 milliseconds, for example.

The electron beam is focused and angled towards the target ring 330. The electron beam is swept over the target ring 330. When the electron beam hits the target ring 330, the target ring 330 emits a fan beam of radiation, such as x-rays, for example. The target ring 330 may be made of tungsten or other metal, for example. The target ring 330 may be shaped in an arc, such as in a 210-degree arc. Each 210-degree sweep of the electron beam over the target ring 330 produces a fan beam, such as a 30-degree fan beam, of electrons from the target ring 330.

The x-rays emitted from the target ring 330 pass through a subject, such as a patient, for example, that is located on the patient positioner 350. The x-rays then impinge upon the detector ring 340. The detector ring 340 may include one, two or more rows of detectors that generate signals in response to the impinging x-rays. The signals are transmitted from the detector ring 340 to the DAS 360 where the signals are acquired and processed.

Data from the detector ring 340 signals may then be sent from the DAS 360 to the image reconstruction module 362. The image reconstruction module 362 processes the data to construct one or more images. The image or images may be stationary image(s), motion image(s), or a combination of stationary and motion (cine) images. The image reconstruction module 362 may employ a plurality of reconstruction processes, such as back projection, forward projection, Fourier analysis, and other reconstruction methods, for example. The image(s) are then transmitted to the image display and manipulation system 364 for adjustment, storage, and/or display.

The image display and manipulation system 364 may eliminate artifacts from the image(s) and/or may also modify or alter the image(s) based on input from the operator console 310 or other image requirements, for example. The image display and manipulation system 364 may store the image(s) in internal or external memory, for example, and may also display the image(s) on a television, monitor, flat panel display, LCD screen, or other display, for example. The image display and manipulation system 364 may also print the image(s). In an embodiment, the manipulation system 364 may be incorporated with the operator console 310. In another embodiment, the manipulation system 364 may be a separate workstation sharing storage with the operator console 310 and/or networked to the operator console 310.

The patient positioner 350 allows a subject, such as a patient, for example, to be positioned between the target ring 330 and the detector ring 340. The patient positioner 350 may be a table, a table bucky, a vertical bucky, a support, or other positioning device, for example. The patient positioner 350 positions the object between the target ring 330 and the detector ring 340 such that x-rays emitted from the target ring 330 after the sweep of the electron beam pass through the object on the way to the detector ring 340. Thus, the detector ring 340 receives x-rays that have passed through the object. The patient positioner 350 may be moved in steps or discrete distances. That is, the patient positioner 350 moves a certain distance and then stops. Then the patient positioner 350 moves again and stops. The stop-and-go motion of the patient positioner 350 may be repeated for a desired number of repetitions, a desired time, and/or a desired distance, for example. Alternatively, the patient positioner 350 may be moved continuously for a desired time, a desired number of electron beam sweeps of the target ring 330, and/or a desired distance, for example, or the patent positioner 350 may not move. In an embodiment, the patient positioner 350 is held still during each scanning maneuver and may be moved to another location for the next maneuver. In another embodiment, the patient positioner 350 may move to allow the system 300 to follow patient lung motion as the patient goes through a lung function maneuver.

In certain embodiments, static and/or dynamic lung measurements may be obtained. Dynamic local lung function may be measured, for example, by measuring the attenuation, or decreasing density, of lung material in a local or selected region of the lung. Patients with diseases such as emphysema may hold air in their lungs longer than healthy people hold air in their lungs. Holding air in the lungs longer than normal is referred to as air trapping. As a result of air trapping, attenuation of lung material as a patient exhales does not increase as rapidly as is typically observed. That is, the more air that is in the lung, the lower the attenuation is. Using lung measurements, various forms of histogram characterization may be performed in local regions of the lung. Additionally, data regarding a portion of the lung may be extracted using a form of contour finding. Change of lung area or change of volume in the lung may also be used to measure local lung function.

Static measurements of local lung function involve measurement of the lung at full inspiration, at full expiration, or at some fixed volume in between with air volume held constant by the spirometer 370. Static measurements of local lung function may be obtained by examining attenuation of lung material, shapes of airways, and/or histogram distributions, for example.

Certain embodiments of the present invention allow local cross-sectional imaging and measurement of local lung function through enhanced sweep speed and programmability. The speed and flexibility of the system 300 allow a range of triggering capabilities and dose choices, for example. That is, image scans may be obtained at various trigger points based on expiration of air from the lungs or on a patient's heart rate (ECG trigger). The system 300 scans rapidly enough to obtain localized images of lung slices during an inspiration and expiration of breath without undue discomfort to the patient.

In operation, cross sectional images may be taken as in a conventional CT or EBT system, for example. An area of a patient lung may be selected based on a low-dose preview or scout scan of the patient. A fast, low x-ray exposure preview scan may be used to obtain a low resolution "map" of the lung. An operator may select a lung area to scan and measure based on the preview information. That is, the preview scan provides information regarding where to position the patient and where to stop and start a scan to obtain an image of the desired area.

In a certain embodiment, the patient is positioned on his or her back on the patient positioner 350. The patient may be positioned on the patient positioner 350 using information from the preview scan. In a certain embodiment, the patient's lung is sampled in multiple locations selected from the preview scan.

In the EBT system 300 the electron beam is swept along the target 330 in a 210-degree arc surrounding the patient at a 90 cm radius, for example. X-rays are generated from the target ring 330 and collimated by the x-ray collimation system 326 into a thin beam irradiating a portion of the patient's lung while the patient is positioned on the patient positioner 350. The x-rays then impact the detector ring 340.

The DAS 360 generates data based on the characteristics of the x-rays impacting the detector ring 340. A plurality of x-rays throughout the lung segment allow an image of the lung cross-section to be generated by the image reconstruction system 362 and/or the image display and manipulation system 364. Prior EBT systems generated image data in 100 ms sweeps. Certain embodiments generate image data in sweeps lasting 50 ms, 33 ms, or less. The resulting image(s) depict lung material and lung characteristics and may indicate onset of a condition in the lung, such as emphysema.

In certain embodiments, the beam control system 320 or other processor is used with the spirometer 370 to measure flow and lung volume as well as to generate a trigger for an imaging sweep. Lung volume is an integral of a volume-time curve over time. Flow is a derivative of the volume-time curve. The trigger from the spirometer 370 is transmitted to the beam control system 320. The beam control system 320 controls the sweep of the electron beam based on the spirometer 370 trigger. The DAS 360 receives image data signals from the detector ring 340 upon x-ray impact. The image reconstruction module 362 reconstructs the cross-sectional images (normal CT behavior) from the image data signals. The image reconstruction system 362 and/or the DAS 360 may measure lung attenuation and extract the contours of the lung. The image display and manipulation system 364 may generate a plot of attenuation versus time, as well as display the cross-sectional lung images.

Air trapping in the lungs appears as a black (low density) region in a cross-sectional image. Local lung function measurements are depicted as a curve of lung material attenuation versus time. Lung function measurement from the spirometer 370 and cross-sectional lung images and data from the DAS 360, image reconstruction system 362, and/or the image display and manipulation system 364 may be combined to improve patient diagnosis and treatment.

Current CT scanners and other cross sectional imaging devices are unable to acquire cross sectional images of a portion of the lung in 100 ms. Lung scans using CT are typically obtained with lung volume held steady at a full inspiration or expiration or at a defined point in between. Such scans may be imprecise and cause patient discomfort if held for an extended period of time. Although an entire lung may be scanned in less than 10 seconds with a modern CT scanner or an EBT scanner, such scans produce static images, not detailed dynamics. Lung function is typically measured with the spirometer 370 measuring how much air is exhaled and how fast. However, these static methods are useful when diseases have advanced in the lungs but these static methods are not sensitive enough to detect early disease, for which intervention (such as with drugs) may be the most beneficial. Certain embodiments of the present invention provide a system and method for cross-sectional imaging of a local lung segment as well as measurement of lung characteristics and function.

Figure 4:
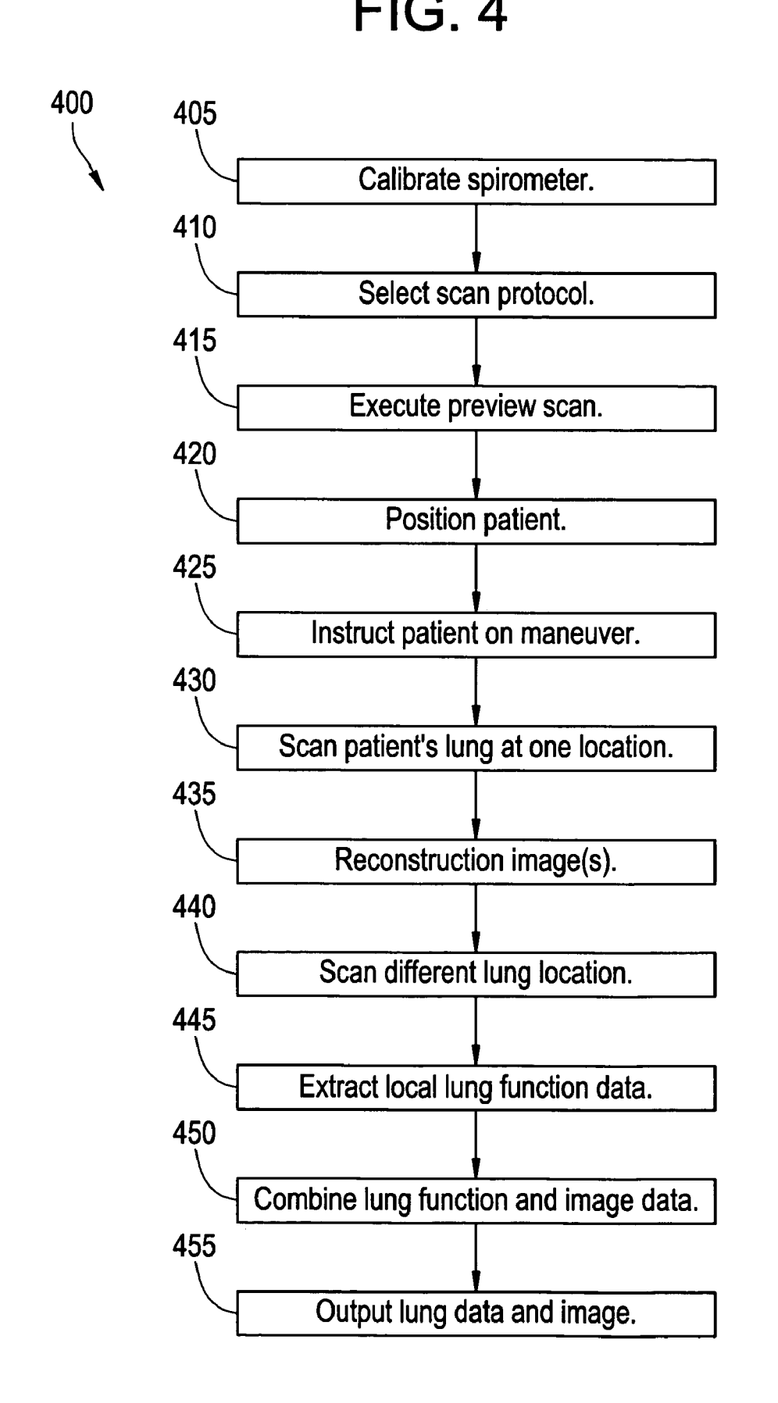
FIG. 4 shows a flow diagram for a method for lung function measurement and localized lung imaging in accordance with an embodiment of the present invention.

FIG. 4 shows a flow diagram for a method 400 for lung function measurement and localized lung imaging in accordance with an embodiment of the present invention. First, at step 405, the spirometer 370 is calibrated with the patient on the patient positioner 350. In an embodiment, the spirometer 370 is calibrated according to a manufacturer's recommendations for use of a "cold" spirometer 370. For example, the spirometer 370 is calibrated with room temperature readings.

Next, at step 410, a scan protocol is selected. For example, a user may select a type of scan to be performed on the CT or EBT scanner. In an embodiment, the protocol is a timed protocol beginning with an external trigger with one or more scans following at prescribed intervals. The protocol may also include a motion specification for the patient positioner 350 to repeat the protocol at set intervals.

Then, at step 415, a preview scan of a patient is executed to obtain an overview of the patient's lung dimensions, position and the like. In a certain embodiment, the preview scan is a low dose scout scan to identify basic layout of the lung in the patient with respect to the system 300. The preview scan may be a localization or scout scan that provides a transmission view of the patient in anterior/posterior and lateral directions, for example. The preview scan may be used to determine at what point to start and stop a localized lung scan. The preview scan may be used to identify which segment or cross-section of the lung to image.

At step 420, the patient is positioned and an image scan configured based on the preview information. The preview scan may help position the patient and the patient positioner 350 in the system 300. Using the preview or scout scan information, a location or locations may be chosen on the patient for a part of the lung to be studied. In an embodiment, the patient positioner 350 moves to the determined position at the beginning of the execution of the selected scan protocol but before the trigger is requested.

Next, at step 425, the patient is instructed regarding a lung maneuver (such as full inspiration and expiration of air, inspiration and breath hold, etc.) to obtain the lung scan. The spirometer 370 connection to the patient may be a tube inserted in the patient's mouth or other device designed to capture air from the patient, for example. The spirometer 370 may include a mask or other casing to help ensure that air is transferred from the patient to the spirometer 370 rather than to the surround environment. The patient is then instructed on how to properly breath to facilitate the lung study. For example, the patient is instructed to take in a full breath or air and let out the air, expelling deeply when instructed. Results may be in the form of a volume-time curve. A threshold may be set and the scan protocol may be modified based on the volume-time curved obtained.

Then, at step 430, a localized region of the patient's lung is scanned. The scan may be triggered by lung volume data read by the spirometer 370 from the patient, by an operator, or by a processor, for example. That is, a trigger from the spirometer 370 may begin a scan sequence that results in image data, such as CT data, obtained at prescribed times in the scan sequence.

At step 435, image(s) are reconstructed from the local lung scan. Multiple cross sectional images may be acquired during a single inspiration/expiration lung maneuver. In a certain embodiment, a series of cross-sectional images may be obtained over a plurality of patient breath holds. Image(s) are obtained by a sweep of an electron beam over the target ring 330, as described above, in a time span of 50 ms, 33 ms, or less, for example. In an embodiment, multiple detector rings may be used to obtain images over a localized region of the lung during the lung maneuver. The image data obtained from the beam sweeps may include an x-ray view in multiple directions. An image showing a cross-sectional view of the lung region may be reconstructed using conventional CT reconstruction techniques, for example.

Next, at step 440, another lung location is scanned. In embodiment, the lung may be sampled in several positions using the same patient maneuver. Local lung positions may be scanned at regular intervals, such as every 10 cm. Local lung positions may also be scanned at positions selected by an operator from information such as a location of branch points of lung airways, for example. Images are then reconstructed from the data obtained, as described above at step 435.

At step 445, local lung function data is extracted. In a certain embodiment, lung function is measured by the spirometer 370. Lung function may be measured before, during, or after an image scan. The spirometer 370 measures the flow of air through the lung and may record changes in flow rate and capacity, for example. In an embodiment, lung measurement may be dynamic and record changes in airflow during an image scan or static and measure lung capacity and air flow at full inspiration and full expiration.

In an embodiment, an area of desired parts of the lung may be extracted from the obtained images. The local lung area is then plotted as a function of time. The plot provides a volume-time curve for a localized region of the lung. The area may be the total area of the lung from a particular sequence. Lung lobe boundaries, for example, may also be used to obtain more localized data. In another embodiment, density of parts of the lung is examined as a function of time. For example, at the end of an expiration of air, the density of the lung should increase (because less air is present). If the lung is not functioning well, air may be trapped in some areas (e.g., not expelled normally), which would result in a density lower than normal. In an embodiment, extraction of lung function data may occur at a workstation. Images may be transferred from the scanner to the workstation for processing and data extraction.

Then, at step 450, lung function measurements may be combined with cross-sectional image data. In a certain embodiment, graphs depicting lung attenuation versus time are paired with lung section images showing air trapping and anomalies in the lung. Additionally, a histogram characterizing the local lung region may be formed and associated with the regional lung image(s). Lung volume and attenuation may also be analyzed in conjunction with airway shapes and lung contours, for example. As an example, a maximum flow rate (a maximum change of area/time from an area-time curve for the lung) for a particular section of an image may be extracted and plotted as a color on, for example, a resting image.

Finally, at step 455, lung data and image(s) may be output (printed, stored, or displayed, for example) for use in patient diagnosis and/or treatment. In an embodiment, extracted data and images are stored to an archival medium, picture archiving and communication system (PACS), or other storage for later retrieval.

For example, in examining a patient's lung, the spirometer 370 is calibrated according to equipment specifications. Room temperature information is used to provide baseline readings for the spirometer 370. Then a flow-time protocol is selected for the EBT scanner 300. The patient being imaged holds a deep breath during a preview scout scan executed to provide an overview of the patient's lung. Then, the patient is positioned using preview data such that the patient's lung is situated for one or more scans of a lung section of interest. Next, a tube from the spirometer 370 is placed in the patient's mouth. The patient inhales deeply and then exhales deeply into the spirometer tube. When the spirometer 370 measures a predetermined air flow threshold, such as 0.5 liter per second, a scan of a lung section is triggered.

Multiple 50 ms scans of the lung occur within several seconds to obtain lung images. During the first second, 50 ms scans are obtained every 100 ms. During the second second, 50 ms scans are executed every 200 ms. Then, during seconds 3-6, scans are executed every 500 ms. The patient is moved or repositioned to scan different lung locations. Alternatively, scans may be 100 ms in duration, for example.

Local lung images are reconstructed from the plurality of scans to provide various cross-sectional images of the lung. The cross-sectional images may be used and/or stored as two-dimensional images. The cross-sectional images may also be combined into three-dimensional image(s). The area of the portion of the lung scanned in each cross-sectional image is determined from the image. Thus, the area of a lung portion at different points in time may be determined from multiple images. The local lung area may be displayed or analyzed as a function of time. Air flow or lung density may also be determined. Obstructions, defects, or other problems with the lung or lung segment may be identified from an analysis of the images and lung function data.

Thus, certain embodiments of the present invention provide a fast, flexible system and method for obtaining lung function measurements and cross-sectional images of lung areas. Certain embodiments use a variety of triggers to provide arbitrary timing between imaging sweeps to obtain data while minimizing patient exposure to x-ray radiation. Certain embodiments allow rapid local lung imaging during patient inspiration and expiration, rather than executing an entire lung scan. Certain embodiments provide local lung imaging to minimize patient discomfort. Certain embodiments allow local lung images to be used with lung function measurements to improve early diagnosis and treatment of lung diseases and improve upon simply measuring lung air flow with a spirometer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for lung imaging, said method comprising:
    triggering a series of image scans, each of a lung cross-section of a patient;
    scanning the plurality of lung cross-sections during at least one of an inspiration and an expiration of air by the patient to obtain lung image data;
    measuring a local lung function during at least one of an inspiration and an expiration of air by the patient to obtain local lung function data;
    reconstructing local lung images from the plurality of lung cross-section scans to provide cross-sectional images of the lung; and
    combining said lung image data from said local lung images and said local lung function data for use in diagnosis of the patient based on an area of a lung portion at different points in time.

2. The method of claim 1, further comprising performing a preview scan of the patient to identify the lung cross-section for imaging.

3. The method of claim 1, further comprising outputting said lung image data and said local lung function data.

4. The method of claim 1, further comprising processing said local lung function data to generate a plot of lung attenuation versus time or area versus time.

5. The method of claim 1, wherein said triggering step comprises triggering said image scan based on air flow in the patient's lung.

6. The method of claim 1, wherein said scanning step dynamically obtains said lung image data as at least one of air flow and air capacity in the lung are changing.

7. The method of claim 1, wherein said scanning step obtains said lung image data with at least one of air flow and air capacity in the lung held constant.

8. The method of claim 1, wherein said scanning step obtains lung image data during a sweep of at most 33 ms.

9. The method of claim 1, wherein said scanning step obtains lung image data during a sweep of at most 50 ms.

10. A diagnostic imaging system, said system comprising:
    a trigger triggering an imaging scan of said patient based on at least one of air flow in said lung, volume of said lung, movement of said lung, and density of said lung;
    an energy source generating an electron beam to strike a target;
    a target producing radiation in response to said electron beam, said radiation irradiating at least a portion of said lung of said patient;
    a detector receiving said radiation after said radiation irradiates said at least a portion of said lung of said patient during said imaging scan;
    a data acquisition system obtaining local lung image data from said detector based on said radiation; and
    a reconstruction system combining local lung function data and said lung image data for use in diagnosis of said patient,
    wherein said system scans a first portion of said lung at a first location and said reconstruction system reconstructs a first image of the lung at the first location, wherein said system scans a second portion of said lung at a second location and said reconstruction system reconstructs a second image of the lung at the second location such that extracted local lung function data is combined with said first and second lung portion images to detect abnormalities in the lung.

11. The system of claim 10, further comprising an output for at least one of displaying, printing, and storing said lung function data and said lung image data.

12. The system of claim 10, wherein said imaging scan comprises an imaging sweep of at most 33 ms.

13. The system of claim 10, wherein said imaging scan comprises an imaging sweep of at most 50 ms.

14. The system of claim 10, wherein said reconstruction system process said lung image data to generate a plot of lung attenuation versus time.

15. The system of claim 10, wherein said data acquisition system dynamically obtains said lung image data as at least one of air flow and air capacity in the lung are changing.

16. The system of claim 10, wherein said data acquisition system obtains said lung image data with at least one of air flow and air capacity in the lung held constant.

17. The system of claim 10, wherein said trigger further triggers a preview scan of said patient to identify said portion of said lung for imaging scan.

18. The system of claim 10, further including a spirometer for measuring function of a lung of a patient, said spirometer generating local lung function data based on at least one of air flow and volume in said lung.

19. The system of claim 18, wherein said trigger triggers said imaging scan based on said local lung function data from said spirometer.

20. method for detecting lung abnormalities in a patient, said method comprising:
    obtaining local lung function data based on at least one of air flow and air volume in a lung;
    triggering a scan of the lung based on the local lung function data;
    scanning a first cross-section of the lung at a first location in a single sweep;
    reconstructing a first image of the lung at the first location;
    scanning a second cross-section of the lung at a second location;
    reconstructing a second image of the lung at the second location; and
    examining the local lung function data in conjunction with the lung cross-section image to detect abnormalities in the lung.

* * * * *